(12) United States Patent
Richter (10) Patent No.: US 8,772,244 B2
(45) Date of Patent: Jul. 8, 2014

(54) TUBULIN INHIBITORS

(75) Inventor: Wolfgang Richter, Martinsried (DE)

(73) Assignee: R&D Biopharmaceuticals GmbH, Martinsreid (DE)

( * ) Notice: Subject to any disclaimer, the term of this patent is extended or adjusted under 35 U.S.C. 154(b) by 162 days.

(21) Appl. No.: 13/509,060

(22) PCT Filed: Nov. 12, 2010

(86) PCT No.: PCT/EP2010/006915
§ 371 (c)(1),
(2), (4) Date: Jun. 18, 2012

(87) PCT Pub. No.: WO2011/057806
PCT Pub. Date: May 19, 2011

(65) Prior Publication Data
US 2012/0252739 A1    Oct. 4, 2012

(30) Foreign Application Priority Data
Nov. 12, 2009   (EP) .................................... 09014170

(51) Int. Cl.
| A61K 38/00 | (2006.01) |
| A61K 38/07 | (2006.01) |
| A61K 38/06 | (2006.01) |
| C07K 5/00 | (2006.01) |
| C07K 7/00 | (2006.01) |
| C07K 16/00 | (2006.01) |
| C07K 17/00 | (2006.01) |
| C07D 277/28 | (2006.01) |
| C07D 211/18 | (2006.01) |

(52) U.S. Cl.
CPC ............ C07D 277/28 (2013.01); C07D 211/18 (2013.01)
USPC .......................... 514/19.3; 514/21.9; 530/331

(58) Field of Classification Search
CPC .. C07D 277/28; C07D 211/18; A61K 31/381; A61K 31/427; A61K 31/435
USPC ................. 514/19.3, 21.9; 530/331
See application file for complete search history.

(56) References Cited

FOREIGN PATENT DOCUMENTS

| CN | 1890218 A | 1/2007 |
| WO | WO 98/13375 | 4/1998 |
| WO | WO 2005/054199 A1 | 6/2005 |
| WO | WO 2008/138561 | 11/2008 |
| WO | WO 2009/012958 | 1/2009 |

OTHER PUBLICATIONS

Dömling et al. "Total Synthesis of Tubulysin U and V" Angewandte Chemie International Edition 2006 45:7235-7239.
Patterson et al. "Design, Synthesis, and Biological Properties of Highly Potent Tubulysin D Analogues" Chemistry—A European Journal 2007 13:9534-9541.
Porstmann et al. "Quantitation of 5-Bromo-2-Deoxyuridine Incorporation into DNA: an Enzyme Immunoassay for the Assessment of the Lymphoid Cell Proliferative Response" Journal of Immunological Methods 1985 82:169-179.
Sasse et al. "Tubulysins, New Cytostatic Peptides from Myxobacteria Acting on Microtubuli. Production, Isolation, Physico-chemical and Biological Properties" The Journal of Antibiotics 2000 53(9):879-885.
International Search Report from PCT/EP2010/006915, Dec. 14, 2010.
International Preliminary Report on Patentability from PCT/EP2010/006914, May 15, 2012.

Primary Examiner — Barbara P Badio
Assistant Examiner — Sara E Townsley
(74) Attorney, Agent, or Firm — Licata & Tyrrell P.C.

(57) ABSTRACT

The present invention relates to novel tubulin binding molecules of formula (I) and their use for the treatment of cancer and other diseases.

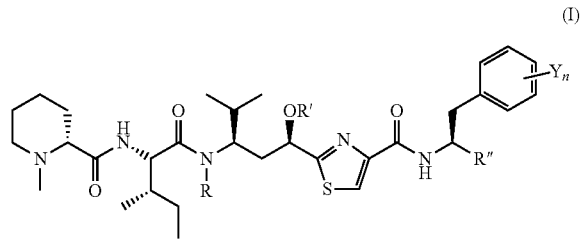

11 Claims, 5 Drawing Sheets

TUBULIN INHIBITORS

This application is a U.S. National Stage Application of PCT/EP2010/006915 filed Nov. 12, 2010, which claims priority from EPO Application No. 090141706 filed Nov. 12, 2009, the contents of each of which are incorporated herein by reference in their entirety.

The present invention refers to novel molecules which inhibit the polymerization of the tubulin skeleton of cancer cells.

It is the objective of the present invention to provide novel cytotoxic molecules which preferably show a high potent activity against cancer cell lines and strong binding affinities to tubulin, thus, being preferably able to kill cancer cells.

The present invention provides one or more compounds of formula (I):

wherein
R is H or an alkyl, alkenyl, alkynyl, CO-alkyl or heteroalkyl group, all of which may optionally be substituted;
R' is H or an alkyl, alkenyl, alkynyl, CO-alkyl or heteroalkyl group, all of which may optionally be substituted;
R" is a group of formula $CH_2OH$ or n is 0, 1, 2, 3, 4 or 5;
Y is independently optionally substituted alkyl (e.g. methyl), heteroalkyl (e.g. MeO), halogen, CN, $NO_2$ or OH;
or a pharmacologically acceptable salt, solvate, hydrate or a pharmacologically acceptable formulation thereof.

The expression alkyl refers to a saturated, straight-chain or branched hydrocarbon group that contains from 1 to 20 carbon atoms, preferably from 1 to 12 carbon atoms, especially from 1 to 6 (e.g. 1, 2, 3 or 4) carbon atoms, for example methyl, ethyl, propyl, isopropyl, isobutyl, n-butyl, sek-butyl, tert-butyl, n-pentyl, 2,2-dimethylpropyl, 2-methylbutyl, n-hexyl, 2,2-dimethylbutyl or 2,3-dimethylbutyl.

The expressions alkenyl and alkynyl refer to at least partially unsaturated, straight-chain or branched hydrocarbon groups that contain from 2 to 20 carbon atoms, preferably from 2 to 12 carbon atoms, especially from 2 to 6 (e.g. 2, 3 or 4) carbon atoms, for example an ethenyl, allyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms (e.g. 1, 2 or 3 hydrogen atoms) have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1, 2 or 3) carbon atoms have been replaced by an oxygen, nitrogen, phosphorus, boron, selenium, silicon or sulfur atom (preferably by an oxygen, sulfur or nitrogen atom). The expression heteroalkyl furthermore refers to a carboxylic acid or to a group derived from a carboxylic acid, such as, for example, acyl (alkyl-CO—), acylalkyl, alkoxycarbonyl, acyloxy, acyloxyalkyl, carboxyalkylamide or alkoxycarbonyloxy.

Preferably, a heteroalkyl group contains from 1 to 12 carbon atoms and from 1 to 4 hetero atoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2 or 3 (especially 1 or 2) hetero atoms selected from oxygen, nitrogen and sulphur (especially oxygen and nitrogen)

Examples of heteroalkyl groups are groups of formulae:
$R^a$—O—$Y^a$—, $R^a$—S—$Y^a$—, $R^a$—N($R^b$)—$Y^a$—, $R^a$—CO—$Y^a$, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$—$Y^a$—, $R^a$—O—CO—O—$Y^a$—, $R^a$—N($R^b$)—C(=N$R^d$)—N($R^c$—$Y^a$—, $R^a$—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ is a hydrogen atom, a $C_1$-$C_6$ alkyl, a $C_2$-$C_6$ alkenyl or a $C_2$-$C_6$ alkynyl group; $R^b$ is a hydrogen atom, a $C_1$-$C_6$ alkyl, a $C_2$-$C_6$ alkenyl or a $C_2$-$C_6$ alkynyl group; $R^c$ is a hydrogen atom, a $C_1$-$C_6$ alkyl, a $C_2$-$C_6$ alkenyl or a $C_2$-$C_6$ alkynyl group; $R^d$ is a hydrogen atom, a $C_1$-$C_6$ alkyl, a $C_2$-$C_6$ alkenyl or a $C_2$-$C_6$ alkynyl group and $Y^a$ is a direct bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by halogen (e.g. fluorine or chlorine) atoms.

Specific examples of heteroalkyl groups are methoxy, trifluoromethoxy, ethoxy, n-propyloxy, isopropyloxy, tert-butyloxy, methoxymethyl, ethoxymethyl, —$CH_2CH_2OH$, —$CH_2OH$, methoxyethyl, methylamino, ethylamino, dimethylamino, diethylamino, isopropylethylamino, methylamino methyl, ethylamino methyl, diisopropylamino ethyl, enol ether, dimethylamino methyl, dimethylamino ethyl, acetyl, propionyl, butyryloxy, acetyloxy, methoxycarbonyl, ethoxycarbonyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The term "optionally substituted" relates to groups, wherein one or more hydrogen atoms have been replaced by fluorine, chlorine, bromine or iodine atoms or by OH, =O, SH, =S, =NH or $NO_2$ groups. This term relates further to groups, which can be exclusively or additionally substituted with unsubstituted $C_1$-$C_6$ alkyl, $C_2$-$C_6$ alkenyl, $C_2$-$C_6$ alkinyl or $C_1$-$C_6$ heteroalkyl groups.

Protecting groups are known to a person skilled in the art and e.g. described in P. J. Kocienski, Protecting Groups, Georg Thieme Verlag, Stuttgart, 1994 and in T. W. Greene, P.

G. M. Wuts, Protective Groups in Organic Synthesis, John Wiley & Sons, New York, 1999. Common amino protecting groups are e.g. t-butyloxycarbonyl (Boc), t-butyldimethylsilyl (TBS), benzyloxycarbonyl (Cbz, Z), benzyl (Bn), benzoyl (Bz), fluorenylmethyloxycarbonyl (Fmoc), allyloxycarbonyl (Alloc), triethylsilyl (TES), trichlorethyloxycarbonyl (Troc), acetyl or trifluoracetyl.

Compounds of formula (I) may comprise several chiral centers depending on their substitution pattern. The present invention relates to all defined enantio- and diastereoisomers as well as their mixtures in all ratios. Moreover the present invention relates to all cis/trans isomers of compounds of general formula (I) as well as their mixtures. Moreover the present invention relates to all tautomeric forms of compounds of the general formula (I).

Preferably, R is H or $C_1$-$C_6$ alkyl; especially a methyl or a propyl group.

Preferably, R' is —CO-alkyl, alkyl or heteroalkyl, especially Acetyl (Ac) or —$CH_2OCH_3$.

Preferably, R" is

Further preferably, R" is —$CH_2OH$.
Preferably, n is 0.
Especially preferred are compounds of formula (I) wherein:
R is $C_1$-$C_6$ alkyl, especially —$CH_3$, ethyl, propyl, butyl, isopropyl, isobutyl, n-pentyl, n-hexyl;
R' is —CO-alkyl or heteroalkyl, especially —CO—$CH_3$ or —$CH_2OCH_3$;
R" is —$CH_2OH$ or (especially —$CH_2OH$) and
n is 0.

Examples of pharmacologically acceptable salts of the compounds of formula (I) are salts of physiologically acceptable mineral acids, such as hydrochloric acid, sulfuric acid and phosphoric acid, or salts of organic acids, such as methanesulfonic acid, p-toluenesulfonic acid, lactic acid, formic acid acetic acid, trifluoroacetic acid, citric acid, succinic acid, fumaric acid, maleic acid and salicylic acid. Further examples of pharmacologically acceptable salts of the compounds of formula (I) are alkali metal and alkaline earth metal salts such as, for example, sodium, potassium, lithium, calcium or magnesium salts, ammonium salts or salts of organic bases such as, for example, methylamine, dimethylamine, triethylamine, piperidine, ethylenediamine, lysine, choline hydroxide, meglumine, morpholine or arginine salts. Compounds of formula (I) may be solvated, especially hydrated. The hydration may take place, for example, during the preparation process or as a consequence of the hygroscopic nature of the initially anhydrous compounds of formula (I). The solvates and/or hydrates may e.g. be present in solid or liquid form.

The therapeutic use of compounds of formula (I), their pharmacologically acceptable salts, solvates and hydrates, respectively, as well as formulations and pharmaceutical compositions also lie within the scope of the present invention.

The pharmaceutical compositions according to the present invention comprise at least one compound of formula (I) as an active ingredient and, optionally, carrier substances and/or adjuvants.

The use of compounds of formula (I) for the preparation of medicaments for the treatment and/or prevention of cancer is also subject of the present invention. Moreover, the present compounds are of interest for the prevention and/or treatment of tumor diseases.

Cancers that can be treated or prevented by the compositions and methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumour, cervical cancer, testicular tumour, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukaemia and acute myelocytic leukaemia (myeloblastic, promyelocytic, myelomonocytic, monocytic and erythroleukemia); chronic leukaemia (chronic myelocytic (granulocytic) leukaemia and chronic lymphocytic Leukaemia), and polycythemia vera, lymphoma (Hodgkin's disease and non-Hodgkin's disease), multiple myeloma. Waldenstrohm's macroglobulinemia, and heavy chain disease.

Other examples of leukaemias include acute and/or chronic leukaemias, e.g., lymphocytic leukaemia (e.g., as exemplified by the p388 (murine) cell line), large granular lymphocytic leukaemia, and lymphoblastic leukaemia; T-cell leukaemias, e.g., T-cell leukaemia (e.g., as exemplified by the CEM, Jurkat, and HSB-2 (acute), YAC 1 (murine) cell lines), T-lymphocytic leukaemia, and T-lymphoblastic leukaemia; B cell leukaemia (e.g., as exemplified by the SB (acute) celline), and B-lymphocytic leukaemia; mixed cellieukaemias, e.g., B and T cellieukaemia and B and T lymphocytic leukaemia: myeloid leukaemias, e.g., granulocytic leukaemia, myelocytic leukaemia (e.g., as exemplified by the HL-60 (promyelocyte) cell line), and myelogenous leukaemia (e.g., as exemplified by the K562 (chronic) celline); neutrophilic leukaemia; eosinophilic leukaemia: monocytic leukaemia (e.g., as exemplified by the THP-1 (acute) celline); myclomonocytic Leukaemia; Naegeli-type myeloid leukaemia; and non-lymphocytic leukemia. Other examples of leukaemias are described in Chapter 60 of The Chemotherapy Sourcebook, Michael C. Perry Ed., Williams & Williams (1992) and Section 36 of Holland Frie Cancer Medicine 5th Ed., Bast et al. Eds., B. C. Decker Inc. (2000). The entire teachings of the preceding references are incorporated herein by reference.

In general, compounds of formula (I) can be given as a single treatment or as multiple treatments either alone or in combination with an arbitrary therapeutic substance according to known and accepted modes or as a continuous treatment whereby the active principle can be embedded in a matrix such as e.g. an implantable hydrogel. Compositions according to the invention can be administered in one of the following ways: orally, including dragees, coated tablets, pills, semi-solids, soft or hard capsules, solutions, emulsions or suspensions; parenteral, including injectable solutions; rectal as suppositories; by inhalation, including powder formulation or as a spray, transdermal or intranasal. For the production of such tablets, pills, semi solids, coated tabletts, dragees and hard gelatine capsules the therapeutically used product is mixed with pharmacologically inert, inorganic or organic carriers, e.g. with lactose, sucrose, glucose, gelatine, malt, silica gel, starch, or derivatives thereof, talkum, stearinic acid or its salts, dried skim milk and the like. For the production of soft capsules one may use carriers like vegetable oils, petroleum, animal or synthetic oils, wax, fat, polyols. For the production of liquid solutions and syrups one may use carriers for example water, alcohols, aqueous saline, aqueous dextrose, polyole, glycerin, vegetable oils, petroleum, animal or synthetic oils. For the production of suppositories one may use excipients like e.g. vegetable, petroleum, animal or synthetic oils, wax, fat and polyols. For aerosol formulations one may use compressed gases suitable for this purpose like e.g. oxygen, nitrogen, noble gas and carbon dioxide. The pharmaceutically useful agents may also contain additives for conservation, stabilisation, e.g. UV stabilizer, emulsifier, sweetener, aromatiser, salts to change the osmotic pressure, buffers, coating additives and antioxidants.

Combinations with other therapeutic agents can include further agents, which are commonly used to treat the diseases mentioned above, especially tumor diseases.

It has been surprisingly found that the compounds of the present invention wherein R" is —CH$_2$OH show the same or a very similar biological activity as the known Tubulysins (see e.g. WO 9813375; F. Sasse, H. Steinmetz, G. Hofle, H. Reichenbach, J. Antibiot. 2000, 53, 879-885; A. W. Patterson et al, Chem. Eur. J. 2007, 13, 9534-9541), although the "Tup" unit has been replaced by a phenylalanine derivative, a much simpler structural unit which is much less complicated to synthesize. The replacement of the "Tup" unit by a derivative of a natural amino acid makes the overall compounds more peptide-like which improves the biodegradability of the compounds in the body. Furthermore, this replacement leads to a reduction of the overall weight of the resulting compounds which leads to an enhanced bioavailability. In addition, the new compounds show an enhanced binding to tubulin.

EXAMPLES

According to the synthetic procedures of the building blocks disclosed herein, compounds of formula (I) were synthesized using common peptide coupling methods known to a person skilled in the art.

Compounds of formula (I) having the following residues where prepared:

R: H, methyl, propyl;
R': Acetyl, —CH$_2$OCH$_3$;
R":—CH$_2$OH;

and
n: 0.

Synthetic Procedures

The syntheses of the respective carbonic acid derivatives of compounds MSRD334, MSRD345 and SDRD28 were performed according to procedures described in PCT/EP2008/003762 (WO 2008/138561). All compounds described in this patent were characterized by 1H-NMR, 13C-NMR and mass spectroscopy. The purity was identified by HPLC.

Synthesis of MSRD368

To a solution of dipeptide (200 mg, 0.44 mmol) in a 1:1 mixture of chloroform/formaldehyde dimethyl acetal (2 mL) P$_2$O$_5$ was added portionwise (626 mg, 4.4 mmol). The reaction mixture was poured into a saturated aqueous solution of NaHCO$_3$ (25 mL) and extracted with AcOEt (1×10 mL). The solvent was removed in vacuo and the crude product was purified by flash chromatography (hexane:AcOEt 7:3) to give 154 mg of MSRD356 (70% yield) as a colorless oil.

MSRD357

To a solution of MSRD356 (144 mg, 0.29 mmol) in a THF/H$_2$O 4:1 mixture (5 mL), LiOH. H$_2$O (19 mg, 0.43 mmol) was added. The reaction was stirred for 5 h, then H$_2$O (10 mL) and AcOEt (10 mL) were added. The layers were separated and a 1 M solution of HCl was added to the aqueous phase until pH 1-2 was reached. The resulting mixture was extracted with AcOEt. The organic phase was dried over anhydrous Na$_2$SO$_4$, filtered and the solvent was removed in vacuo to give 119 mg of pure MSRD357 (87% yield) as a white solid.

MSRD360

To a solution of MSRD357 (109 mg, 0.23 mmol) in DMF (5 mL), HOAt (38 mg, 0.28 mmol), HATU (105 mg, 0.28 mmol) and Et$_3$N (70 µL, 0.51 mmol) were added. After stirring for 5 min Tup (55 mg, 0.25 mmol) was added. The reaction mixture was stirred for 2 h. The reaction was diluted with H$_2$O (10 mL) and extracted with Et$_2$O (1×10 mL). The organic phase was washed with a 1N aqueous solution of HCl (1×15 mL), with a saturated aqueous solution of NaHCO$_3$ (1×15 mL) and with brine (2×15 mL). After drying over anhydrous Na$_2$SO$_4$, and filtration, the solvent was removed in vacuo to give 159 mg of pure MSRD360 (quantitative yield) as a white foam.

MSRD362

To a solution of MSRD360 (149 mg, 0.22 mmol) in MeOH (5 mL), Pd/C was added. The reaction mixture was stirred 18 h under a hydrogen atmosphere. The reaction was filtered through celite and the filtrate was concentrated under reduced pressure to give 142 mg of pure MSRD362 as white foam in quantitative yield.

MSRD364

To a suspension of N-Methylpipecolinic acid (34 mg, 0.24 mmol) in DCM (5 mL), HOAt (35 mg, 0.26 mmol), HATU (99 mg, 0.26 mmol), Et$_3$N (67 µL, 0.48 mmol) and MSRD362 (142 mg, 0.22 mmol) were added. The reaction mixture was stirred for 4 h. The reaction was washed with H$_2$O (10 mL), with a saturated aqueous solution of NaHCO$_3$ (1×15 mL) and with brine (1×15 mL). After drying over anhydrous Na$_2$SO$_4$, and filtration, the solvent was removed in vacuo. The crude was purified by FC (DCM:MeOH 97:3) to give 107 mg of MSRD364 (63% yield) as a white foam.

MSRD365

To a solution of MSRD364 (102 mg, 0.13 mmol) in THF (5 mL), a 1N aqueous solution of LiOH (400 µL, 0.40 mmol) was added. The reaction was stirred for 2 days and then acidified with TFA until pH 1-2 was reached. The resulting mixture was washed with H$_2$O (5 mL) and extracted with AcOEt (10 mL). The organic phase was basified with Et$_3$N until pH 8 was reached, washed with H$_2$O (5 mL), dried over anhydrous Na$_2$SO$_4$, filtered and the solvent was removed in vacuo. The residue was purified by flash chromatography (DCM/MeOH 9:1), affording 52 mg of MSRD365 (52% yield) as a white foam. The reduction of MSRD365 towards MSRD368 was done according to the general procedure described below.

Synthesis of MSRD390

MSRD371

-continued

To a solution of phenylalaminole 300 mg, 1.98 mmol) in DCM (10 mL), cooled at 0° C., Et$_3$N (414 µL, 2.97 mmol), imidazole (269 mg, 3.96 mmol) and TBDPCl (516 µL, 1.98 mmol) were added. The reaction mixture was warmed to r.t., stirred overnight and quenched with water (5 mL). The layers were separated and the organic phase dried over anhydrous Na$_2$SO$_4$, filtered and the solvent was removed in vacuo. The residue was purified by flash chromatography (DCM/MeOH 97:3, DCM/MeOH 95:5), affording 647 mg of MSRD371 (84% yield) as a colorless oil.

MSRD379

To a solution of dipeptide (85 mg, 0.20 mmol) in DMF (5 mL) HOAt (33 mg, 0.24 mmol), HATU (91 mg, 0.24 mmol), Et$_3$N (61 μL, 0.44 mmol) and MSRD371 (93 mg, 0.24 mmol) were added. The reaction mixture was stirred for 4 h and 20 mL Et$_2$O were added. The reaction was washed with H$_2$O (10 mL), with a saturated aqueous solution of NaHCO$_3$ (1×15 mL) and with brine (1×15 mL). After drying over anhydrous Na$_2$SO$_4$, and filtration, the solvent was removed in vacuo to give 157 mg of pure MSRD379 (quantitative yield) as a white foam.

MSRD380

To a solution of MSRD379 (149 mg, 0.19 mmol) in DCM (10 mL) Ac$_2$O (76 μL, 0.93 mmol), pyridine (45 μL, 0.47 mmol) and a catalytic amount of DMAP were added. The reaction mixture was stirred for 3 h and the solvent was removed in vacuo. The residue was purified by flash chromatography (Hex/AcOEt 7:3) to give 143 mg of MSRD380 (89% yield) as a white foam.

MSRD388

To a solution of MSRD380 (133 mg, 0.16 mmol) in MeOH (5 mL) Pd/C was added. The reaction mixture was stirred 18 h under a hydrogen atmosphere. The reaction was filtered through celite and the filtrate was concentrated under reduced pressure to give 124 mg of pure MSRD388 (95% yield) as white foam.

MSRD389

To a suspension of N-Methylpipecolinic acid (33 mg, 0.23 mmol) in DCM (5 mL) HOAt (33 mg, 0.24 mmol), HATU (91 mg, 0.24 mmol), Et$_3$N (54 μL, 0.39 mmol) and MSRD388 (124 mg, 0.15 mmol) were added. The reaction mixture was stirred for 4 h. The reaction was washed with H$_2$O (10 mL), with a saturated aqueous solution of NaHCO$_3$ (1×15 mL) and with brine (1×15 mL). After drying over anhydrous Na$_2$SO$_4$, and filtration, the solvent was removed in vacuo. The crude product was purified by flash chromatography (DCM:MeOH 97:3) to give 100 mg of MSRD389 (71% yield) as a white foam.

To a solution of the corresponding carbonic acid derivative (0.04 mmol) in THF (2 mL), Et$_3$N (7 μL, 0.05 mmol) was added. After cooling the reaction mixture to 0° C., EtOCOCl (5 μL, 0.05 mmol) was added. The reaction was stirred at the same temperature for 30 min and filtered through celite. The solution was then added to a solution of NaBH$_4$ (3.0 mg, 0.08 mmol) in water (1 mL) and cooled at 0° C. The reaction mixture was stirred at the same temperature for 30 min, quenched with H$_2$O (5 ml) and extracted with EtOAc (1×5 mL). The solvent was removed in vacuo and the crude product To a solution of MSRD389 (89 mg, 0.09 mmol) in THF (3 mL) a 1M solution of Bu$_4$NF in THF (189 μL, 0.189 mmol) was added. The reaction mixture was stirred for 4 min and washed with water (5 mL). The aqueous phase was extracted with AcOEt (1×10 mL). The collected organic phases were dried over anhydrous Na$_2$SO$_4$, filtrated and the solvent was removed in vacuo. The crude product was purified by flash chromatography (DCM:MeOH 97:3, 93:7) to give 59 mg of MSRD390 (94% yield) as a white foam. All analytical data (HNMR, CNMR, MS) correspond to the structure of MSRD390.

General Procedure for the Reduction of the Carbonic Acid Derivatives MSRD334, MSRD345, MSRD368 and SDRD28:

was purified by flash chromatography (DCM:MeOH 94:6) to give 24 mg of the corresponding alcohol (81% yield) as a white foam.

Determination of the IC-50 Concentration Against Various Cancer Cell Lines

The activity of some representative example compounds of the present invention has been determined with the BrdU-Assay as described in: Porstmann T., Ternynck T., Avrameas S. (1985) "Quantification of 5-bromo-2-deoxyuridine incorporation into DNA: an enzyme immunoassay for the assessment of the lymphoid cell proliferative response." *J. Immunol. Methods* 82: 169-179.

The results are shown in Table 1.

TABLE 1

| Compound | IC50 cell line [nM] | | | | | |
| --- | --- | --- | --- | --- | --- | --- |
| | HCT-116 | Skov-3 | MCF-7 | MCF-7 MX100 | MCF-7 TX200 | MCF-7 VP |
| MSRD334 | 1.06 | 1.05 | 0.57 | 0.62 | 15.55 | 0.88 |

TABLE 1-continued

| Compound | | IC50 cell line [nM] | | | | | |
|---|---|---|---|---|---|---|---|
| | | HCT-116 | Skov-3 | MCF-7 | MCF-7 MX100 | MCF-7 TX200 | MCF-7 VP |
| (structure) | MSRD345 | 1.35 | 1.18 | 0.40 | 0.28 | 50.56 | 1.20 |
| (structure) | MSRD368 | 41.06 | 29.91 | 3.91 | 4.01 | 322.3 | 6.38 |
| (structure) | MSRD390 | 1.10 | 1.06 | 0.27 | 0.20 | 24.41 | 0.54 |
| (structure) | SDRD28 | 4.31 | 3.35 | 0.55 | 1.41 | 370.2 | 3.04 |

In general the new molecules of the present invention show an activity against several cancer cell lines between 0.1 to 400 nM.

Figure 1:
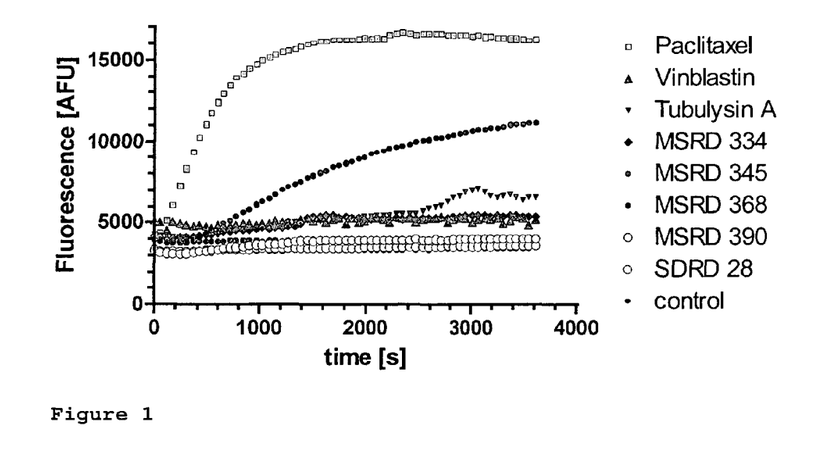
Figure 2A:
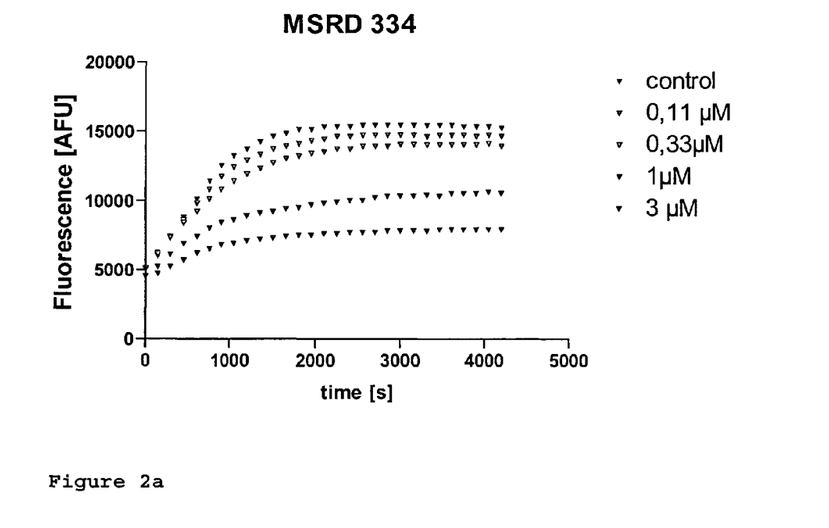
Figure 2B:
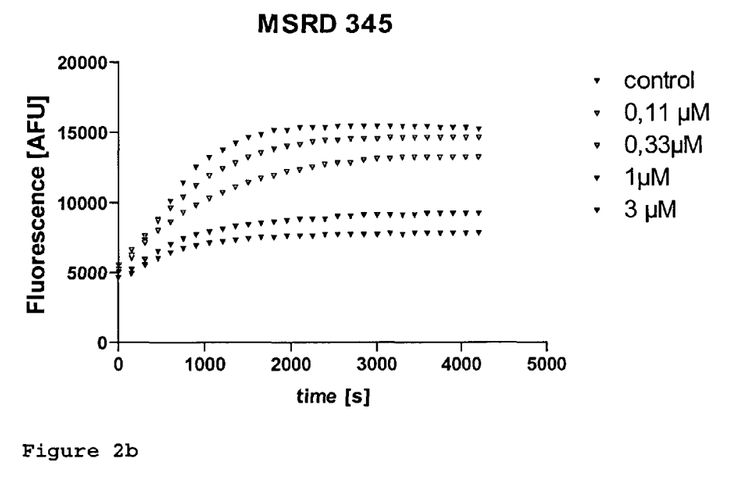
Figure 2C:
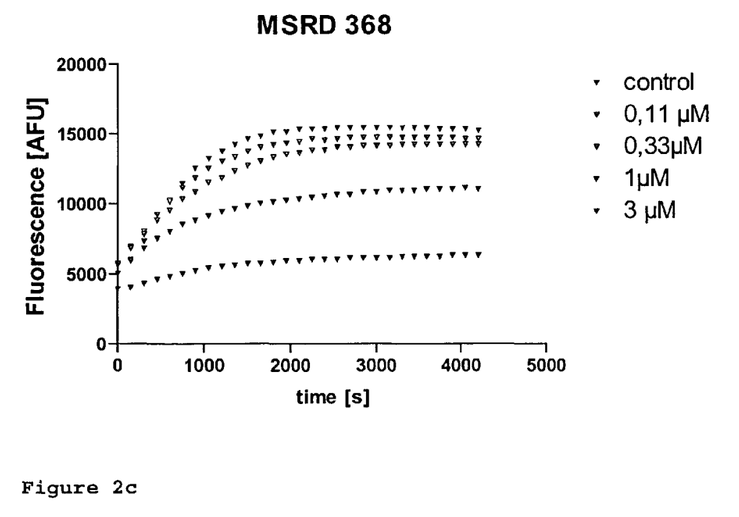
Figure 2D:
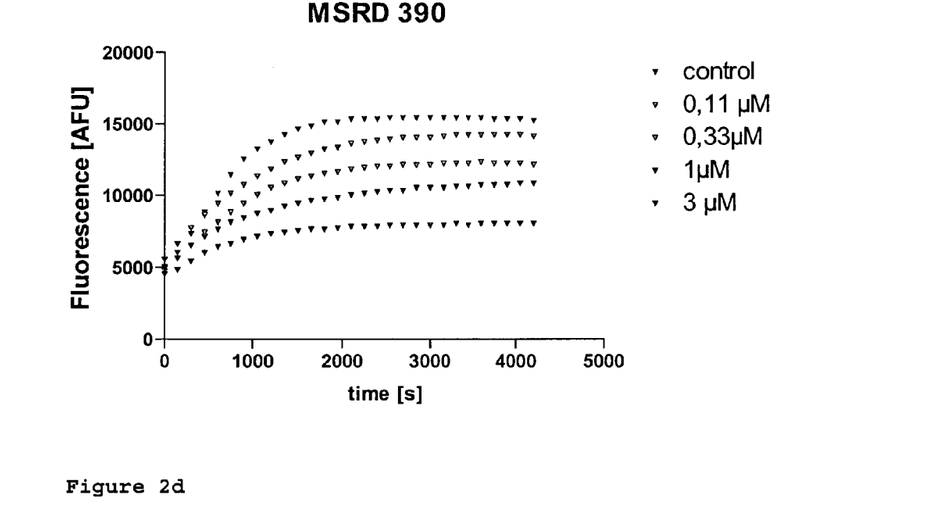
Figure 2E:
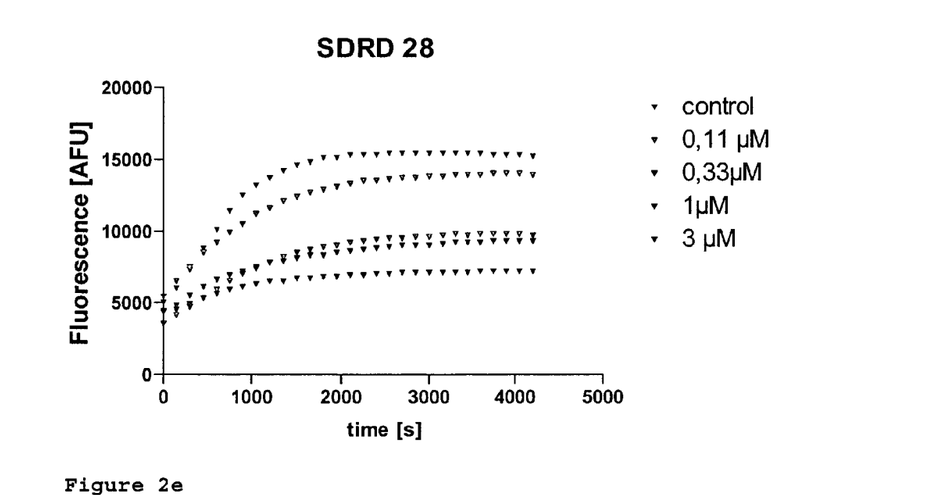

Determination of the Destabilisation Effect Against Microtubuli (FIG. 1)

FIG. 1 shows the destabilising effect against microtubuli. To proof that the novel compounds according to formula (I) are showing an destabilizing effect against microtubuli the in vitro activity was measured in an tubulin polymerisation assay. As controls a tubulin stabilising agent (taxol) and strong destabilising agents (vinblastin and tubulysin A) were used. The novel compounds show an remarkable destabilising effect against microtubuli like e.g. vinblastin.

Determination of the Concentration Dependency of the Microtubuli Polymerisation

FIGS. 2a-e show the concentration dependency in the microtubuli polymerisation assay. A clear concentration dependent effect against microtubuli polymerisation was determined.

Determination of the In-Vitro Activity in the Tubulin Polymerisation Assay

Figure 3A:
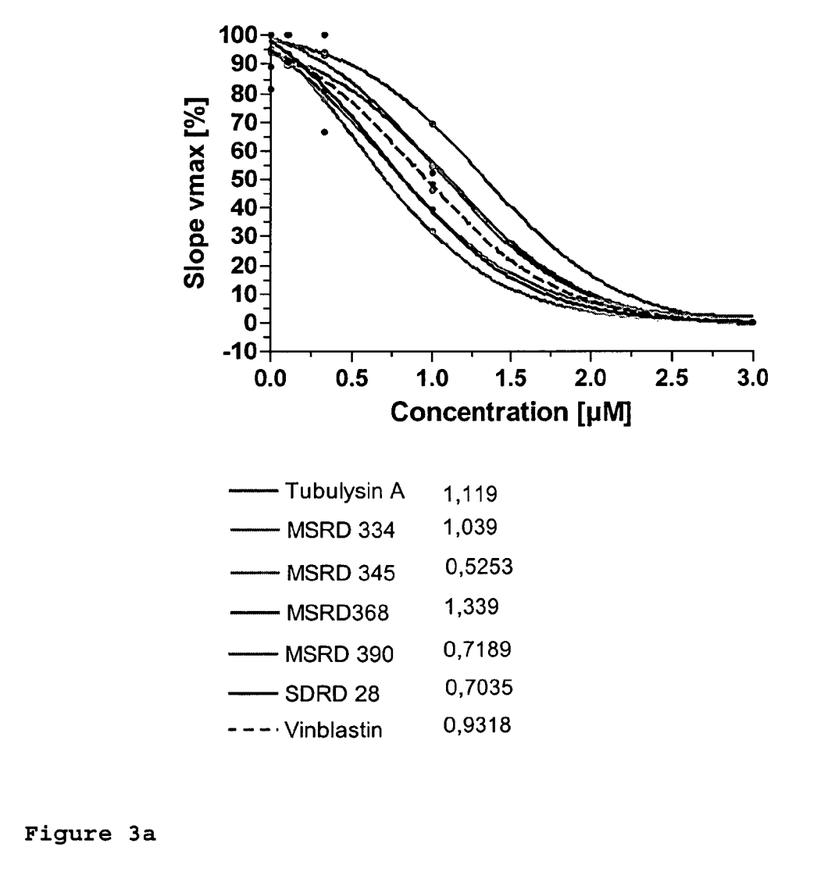
Figure 3B:
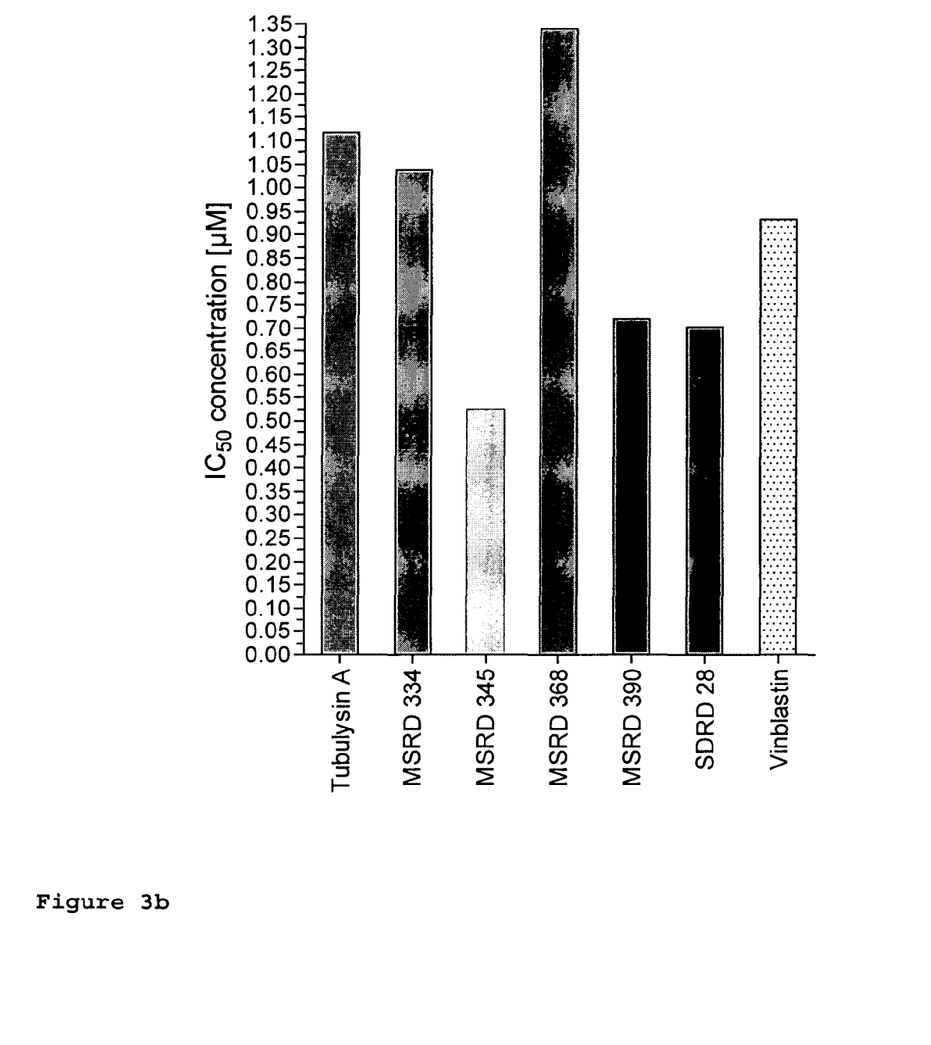

FIGS. 3a-b shows the IC-50 concentration against tubulin polymerisation. The IC-50 concentration of the activity against the tubulin polymerisation was determined and compared to strong inhibitors of the micrtubuli skeleton like e.g. vinblastin, tubulysin A.

The invention claimed is:

1. Compound of formula (I):

(I)

wherein
R is H or an alkyl, alkenyl, alkynyl, CO-alkyl or heteroalkyl group, all of which may optionally be substituted;
R' is H or an alkyl, alkenyl, alkynyl, CO-alkyl or heteroalkyl group, all of which may optionally be substituted;
R" is a group of formula —CH$_2$OH or n is 0, 1, 2, 3, 4 or 5;

Y is independently optionally substituted alkyl, heteroalkyl, halogen, CN, NO$_2$ or OH;

or a pharmacologically acceptable salt, solvate, hydrate or a pharmacologically acceptable formulation thereof.

2. Compound according to claim 1 wherein R is H or C$_1$-C$_6$ alkyl.

3. Compound according to claim 1, wherein R' is —CO-alkyl, alkyl or heteroalkyl.

4. Compound according to claim 1, wherein R" is

5. Compound according to claim 1, wherein R" is CH$_2$OH.

6. Compound according to claim 1, wherein n is 0.

7. Compound according to claim 1 wherein R is C$_1$-C$_6$ alkyl, R' is —CO-alkyl or heteroalkyl, n is 0 and R" is —CH$_2$OH or 8. Compound according to claim 1 wherein R is methyl, R' is acetyl, n is 0 and R" is 9. Pharmaceutical composition containing a compound according to claim 1 and optionally one or more carriers or adjuvants.

10. A method for treating cancer comprising administering a compound of claim 1 to a subject in need thereof, thereby treating the subject's cancer.

11. A method for treating cancer comprising administering a pharmaceutical composition of claim 9 to a subject in need thereof, thereby treating the subject's cancer.

* * * * *

UNITED STATES PATENT AND TRADEMARK OFFICE
CERTIFICATE OF CORRECTION

PATENT NO. : 8,772,244 B2  Page 1 of 1
APPLICATION NO. : 13/509060
DATED : July 8, 2014
INVENTOR(S) : Wolfgang Richter It is certified that error appears in the above-identified patent and that said Letters Patent is hereby corrected as shown below:

On the Title Page,

Item (30) delete "09014170"
Item (30) add --090141706--

Signed and Sealed this
Fourth Day of November, 2014

Michelle K. Lee
*Deputy Director of the United States Patent and Trademark Office*